(12) United States Patent
Pell

(10) Patent No.: US 8,225,795 B2
(45) Date of Patent: Jul. 24, 2012

(54) KINK RESISTANT ENDOTRACHAEL TUBE

(76) Inventor: Donald M. Pell, St. Pete, FL (US)

(*) Notice: Subject to any disclaimer, the term of this patent is extended or adjusted under 35 U.S.C. 154(b) by 381 days.

(21) Appl. No.: 12/568,230

(22) Filed: Sep. 28, 2009

(65) Prior Publication Data
US 2011/0073113 A1    Mar. 31, 2011

(51) Int. Cl.
*A61M 11/00* (2006.01)
(52) U.S. Cl. ............................. 128/207.15; 128/207.16
(58) Field of Classification Search ............ 128/207.15, 128/207.14, 200.26, 207.16; 604/101.01, 604/96.01, 102.02
See application file for complete search history.

(56) References Cited

U.S. PATENT DOCUMENTS

| | | | |
|---|---|---|---|
| 4,305,392 A | 12/1981 | Chester | |
| 4,632,108 A * | 12/1986 | Geil | 128/207.14 |
| 4,840,173 A | 6/1989 | Porter, III | |
| 5,020,534 A * | 6/1991 | Pell et al. | 128/207.15 |
| 5,067,497 A | 11/1991 | Greear et al. | |
| 5,143,062 A | 9/1992 | Peckham | |
| 5,311,864 A | 5/1994 | Huerta | |
| 5,520,175 A | 5/1996 | Fry | |
| 6,062,223 A * | 5/2000 | Palazzo et al. | 128/207.15 |
| 7,089,942 B1 | 8/2006 | Grey | |
| 7,270,647 B2 | 9/2007 | Karpowicz et al. | |
| 7,654,264 B2 * | 2/2010 | Clayton | 128/207.15 |
| 2002/0195110 A1 * | 12/2002 | Watton | 128/207.15 |

* cited by examiner

*Primary Examiner* — Steven Douglas
(74) *Attorney, Agent, or Firm* — Lowe Hauptman Ham & Berner LLP

(57) ABSTRACT

A kink resistant silicon endotracheal tube includes an inflatable cuff for positioning the endotracheal tube in a patient's trachea. The cuff is folded over onto itself to provide a cavity for accumulating bacteria and secretions that are then removed by suction. The cuff in the lower part of the endotracheal tube is also folded over onto itself for centering the endotracheal tube in the center of an airway. A suction catheter is also positioned in a portion of the tube under tension as opposed to a portion under compression to reduce the likelihood of kinking. A kink resistant endotracheal tube also includes a thickened and/or reinforced area of the curved portion of the endotracheal tube in an area under compression.

9 Claims, 2 Drawing Sheets

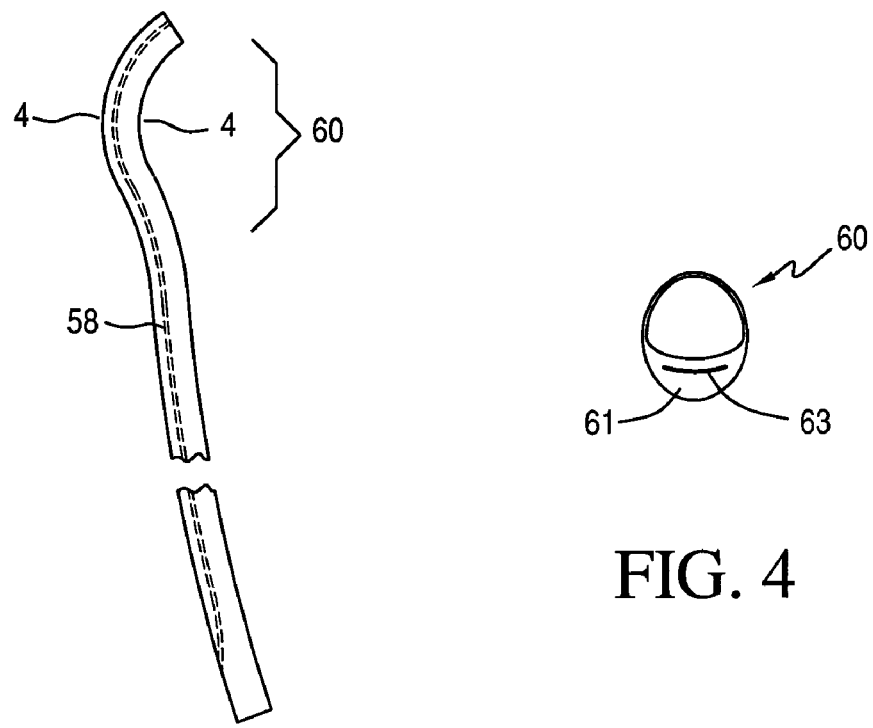
FIG. 3
FIG. 4
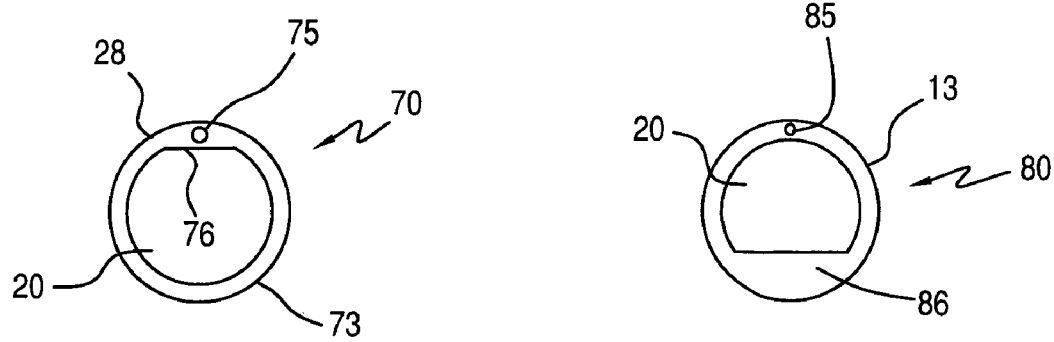
FIG. 5a
PRIOR ART
FIG. 5b

KINK RESISTANT ENDOTRACHAEL TUBE

FIELD OF THE INVENTION

This invention relates to a kink resistant endotracheal tube and more particularly to a kink resistant endotracheal tube having an improved cuff for positioning the endotracheal tube into a patient's trachea and for pooling and suctioning off secretions and bacteria that accumulates above the cuff.

BACKGROUND FOR THE INVENTION

Endotracheal tubes are frequently used for the primary purpose of ensuring that a patient's airway remains clear, which secondarily provides access to the bronchial tree for the aspiration of secretions. However, due the fact that the intubation device is a tube placed within the body passageway, the natural lumen or size thereof is necessarily reduced, although the narrower tube lumen is expected to be clear. This leads to a specific problem. The problem is that most if not all conventional endotracheal tubes kink when subjected to normal body temperature which significantly increases the work of breathing. An inflatable cuff near a distal end of the intubation device is inflated once the tube is intubated for holding the tube in place. The inflatable cuff seals the tube to the body passageway so that all of the air passing to and from the patient's lungs must pass through the tube. The inflated cuff, in position, also forms a space above the cuff and between the intubation device and the body passageway within which secretions and bacteria, or the like, will accumulate. The seal of the inflatable cuff advantageously prevents the accumulated secretions from passing into the patient's lungs so long as the cuff remains fully inflated. Nevertheless, the secretions that build up within this space may cause harm to the patient.

For the above reason, a suction tube is included to remove the secretions and bacteria that collect above the cuff. Then, when the intubation device is intubated within the respiratory tract, the tube passes into the trachea through the epiglottis and as a result the epiglottis cannot then close. Thus, the salvia from the mouth can pass and become trapped in the larynx and trachea. Moreover, other secretions that are produced by the body are trapped as well. The large amount of secretions and bacteria that collect in the space above the cuff could be drawn into the patient's lungs during coughing, cuff deflation, or extubation (i.e. tube removal). This not only presents an immediate danger to the patient's ability to breath, but is believed to substantially increase the chance that the patient will develop aspiration pneumonia.

Thus, it has become desirable to find ways for removing the secretions and bacteria that collect above the cuff during the time period of intubation. Typically, such removal includes the application of suction to the above-the-cuff region for the removal of collected secretions. The initial solution was simply to periodically insert a suction catheter along with the intubation device once intubated and sealed by the cuff to suction out accumulated secretions. As a modification to this procedure, it is presently known to provide an intubation device including an integrally formed suction catheter with an opening in and above-the-cuff region through which periodic or constant suction can be applied for removal of secretions after intubation located on the greater or outer side of the tube.

An improved intubation device is disclosed in my earlier U.S. Pat. No. 5,697,365, which is incorporated herein in its entirety by reference. As disclosed in my earlier U.S. Patent there are many types of endotracheal tubes known to the medical profession and many types of known apparatus for keeping the tubes in place in a patient's oral cavity and trachea. However, it is has been found that a number of these tubes may have life threatening consequences. One of the most serious consequences is the deficiencies of the materials selected for use in the manufacturing of the tubing. Some of the plastic materials used for making endotracheal tubing are not heat stable in their physical characteristics at body temperature and do not remain firm enough at those temperatures to retain their desired shapes while being inserted and while in place. Sometimes the tubing will collapse and/or kink significantly reducing the rate of flow of air, oxygen mixture, etc. that can flow through the tube. The total volume of fluid flow per unit of time through a tube is give by Poiseuille's law as follows:

$$\frac{dV}{dt} = \frac{\pi}{8} \frac{R^4}{n} \frac{(p_1 - p_2)}{L},$$

where
V=Volume of flow.
R=radius of the tube
p1 and p2 are the pressures at the respective ends of the tube.
N=viscosity of the flowing fluid.
L=the length of the tube.

$\frac{dV}{dt}$ is $\frac{\text{rate of flow}}{\text{change in time}}$

From this equation it is seen that any slight restriction in the radius R of the tube can have a significant reduction in the rate of flow through the tube since the radius is raised to the fourth power and adversely affects the work of breathing.

Additionally, it is seen that the rate of flow is inversely proportional to the length of the tube. Therefore, for a weak patient who does not have the strength to overcome any significant resistance to breathing, not only must the tube remain uniform in cross section throughout its length, but the tube must be as, short as possible.

Additionally as disclosed in my earlier patent, an endotracheal tube construction includes an elongated kink resistant flexible tubular member having distal and proximal ends with a curved portion there between. The tubular member defines a major passageway or airway and a relatively small cuff inflating lumen which is parallel to a major passageway and disposed at the end of the tubular member. The cuff inflating lumen is positioned within a portion of the wall which is subjected to tension (the greater curvature) as the tubular member is bent as opposed to being positioned in the portion of the wall that is under compression (the lesser curvature). In addition, the portion of the wall adjacent to the lumen may be thicker than the wall in other portions of the tube, a D-shaped reinforcement so that the tube is less likely to kink or collapse during intubation of a patient.

The endotracheal tube preferably includes a bevel tip and is constructed and arranged so that the bevel tip can be rotated by twisting a portion of the tube which extends out of a patient's mouth or nose without kinking or collapsing the tube. In this way, the far end of the suction catheter can be biased in the direction of the selected bronchi. A second minor passageway or lumen is also parallel to a central passageway and disposed in the same portion i.e. (the wall of greater curvature) of the tubular member.

Notwithstanding the above, it is presently believed that there is a need and a potential commercial market for an improved endotracheal tube and inflatable cuff with an improved construction. There should be a need and a commercial market for such endotracheal tubes because they are properly centered and facilitate accumulation and removal of bacteria and secretions from above the cuff. In addition, such tubes are durable and less likely to kink then conventional tubes. Further, the construction of the cuff not only facilitates the centering of the tube but reduces the likely hood of the tapered end being off center. Still further, the endotracheal tube has a reinforced side on the portion of lesser curvature to prevent or at least reduces the likelihood of kinking.

BRIEF SUMMARY OF THE INVENTION

In essence, a kink resistant endotracheal tube with an inflatable cuff for positioning the endotracheal tube in a patient's trachea comprises or consists of a flexible elongated tubular member having distal and proximal open ends. The tubular member also includes a curved portion between the distal and proximal ends and defines a central major passageway for ventilation of a patient.

The tubular member preferably includes a first minor passageway and an inflatable cuff for centering the tubular member in a patient's trachea and for accumulating or removing secretions above the cuff. The inflatable cuff is of a gas impervious material such as silicone that is secured to an outer surface or exterior surface of the hollow tube at a distal end and at a short distance above the distal end. An important feature of the present invention resides in an upper portion of the inflatable cuff being folded back upon itself (FIG. 1) so that when inflated it bellows out away from the tubular member to form a concave surface for accumulating secretions. Another feature of the construction resides in the curved portion that defines an inner pathway wherein the tubular member is under compression (the lesser curvature) and an outer pathway (the greater curvature) wherein the tubular member is under tension. In the present construction, two minor passageways are in the outer wall of the tubular member, one for inflating the cuff, the other for suctioning off secretions, both of which are in the area under tension while the cuff is folded back upon itself at the upper and lower portions of the cuff and the distal end of the cuff is also folded over upon itself for positioning the end of the tube in the center of the trachea.

An important aspect of the present invention resides in a kink resistant tube. For example, in a preferred embodiment of the invention, the tube is made of silicone which is resistant to kinking at body temperature while tubes of other materials kink as the temperature approaches 100° F. Further, the preferred embodiment of the invention has a thickened wall section and more preferably an internal D-shaped cross-section of that portion of the tube with the shorter or sharper (inner) radius of curvature i.e. is under compression. It is also believed that a thin strip of reinforcing material, can be used particularly in tubes that are made of other materials such as polyethylene, polyvinyl chloride etc.

An important feature of one embodiment of the invention is illustrated in FIGS. 3 and 4. As shown, the endotracheal tube includes a curved portion 60 that includes a thickened wall portion 61. The thickened portion 61 and/or reinforcing strip is in the area of the curved portion that is under compression and which has the sharper curve or shorter radius of curvature.

The invention will now be described in connection with the accompanying drawings.

DESCRIPTION OF THE DRAWINGS

FIG. 3 is a schematic side view illustrating a curved portion of an endotracheal tube with a thickened wall in the area under compression;

FIG. 4 is a cross-sectional view along line 4-4 of FIG. 3; and

FIG. 5a is a cross-sectional view of a prior art endotracheal tube; and

FIG. 5b is a cross-sectional view of an endotracheal tube in accordance with the present invention.

DESCRIPTION OF THE PREFERRED EMBODIMENTS OF THE INVENTION

Figure 1:
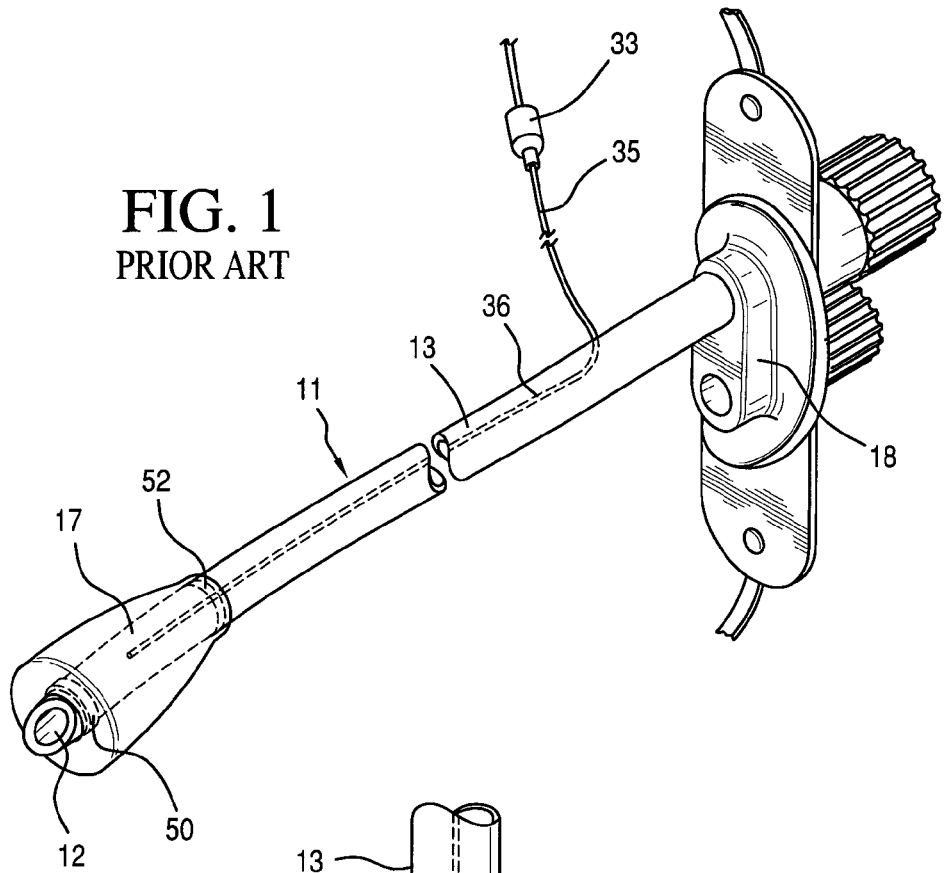
FIG. 1 is a schematic illustration of an endotracheal tube in accordance with my earlier invention as described in my U.S. Pat. No. 5,697,365.

As shown in FIG. 1, an endotracheal tube 11 includes a length of tubing or tubular member 13 having a distal end portion 17 which is constructed and arranged for oral intubation in a patient's trachea as will be described hereinafter. The tubular member 13 also includes a proximal end portion 16 which passes through a patient's mouth and into and through a bite block 18.

The tubular member 13 is sufficiently flexible to bend and conform to a patient's anatomy but may include a permanent bend which generally conforms to the anatomical curve between the oral cavities and the trachea. Those tubes which include a permanent curved section are still somewhat flexible in that portion in order to conform to the anatomical curve of a specific patient. However, in either case the tubing has the physical properties which are selected to reduce the likelihood of kinking or collapsing during insertion and while in place as will be described below.

The tubular member 13 should be able to bend to substantially 90 degrees without the wall collapsing or kinking. The problem is that the tube is more likely to kink or collapse at body temperature. For this reason the presently preferred tubing is made from a medical grade silicon material so that the physical characteristics of the tube are relatively stable at human body temperature. Such characteristics include a hardness in the range of about 80 durometer. In one size of tubing, made for oral intubation, the inner diameter is 0.32 inches (8 mm) and the wall thickness is about 0.040" (1 mm). These dimensions are representative.

A presently preferred composition of silicone has the following constituent materials and approximate proportions by weight.

| | |
|---|---|
| Dimethyl Silicone | 90% |
| Inert Silica Filler | 10% |
| Platinum Salts as catalyst or curing agent | less than 1% |

Conventional mixing, exchanging and curing methods may be used and are well know to those skilled in the art.

Although the above described silicone material is presently preferred, other materials having the described characteristics, i.e. a durometer of about 80 may be used. For example, a medical grade bio-compatible polyurethane, polyethylene, or other material may be used if a sufficient durometer rating can be obtained. In essence, it is important that the physical characteristics of the material are selected to provide sufficient stiffness and resistance to kinking with a minimum wall thickness. Thus, in selecting the wall thickness and physical characteristics of material, care should be exercised in constructing a tube which will not kink at normal human body temperatures and which allows the tip of the tubular member to be rotated by twisting the portion of the tube which extends out of the mouth or nose of a patient. For example, in prior art tubes there is sufficient stiffness at human body temperature to transmit the torque from one end of the tube to the other. If the stiffness is insufficient, it would be like twisting a piece of hot spaghetti. If the tubes are too rigid it is not possible to rotate the tip by twisting the end because the anatomical arch prevents the rotation of the tube. The ability to rotate is important in order to duct secretions and reduce the work of breathing.

Tubular member 13 is of one piece, extruded construction and has a smooth exterior and interior surface throughout. The distal end 12 of the tubular member 13 usually is cut diagonally i.e. at an acute angle to the central axis of the tube. The tubular member 13 is somewhat flexible and conforms to the patient's anatomy when inserted. It is characteristic of a tube of this invention that it will not kink or collapse while being intubated or after being in place for great lengths of time. It should be recognized that it is also important that the minor passageways do not kink or collapse since that would negate working of suction. The distal portion 16 of the endotracheal tube is provided with an expandable cuff of the lumen 31 of a gas impervious material such as a thin sheet of silicone material of the type described above. Cuff 31 is inflated by means of a pilot balloon 33 connected to the cuff by an external minor tube 35 and internal passage 36 in the wall (of greater radius) of the tubular member 13. When the cuff 31 is inflated to engage the wall of tracheal 19 air or other gas is passed to and from the patient's lungs (not shown) through the bronchi and through the interior of the tubular member 13. The proximal end 16 and the tubular member 13 is adapted to be connected to a ventilator or oxygen source and/or a suction device in a normal manner.

Figure 2:
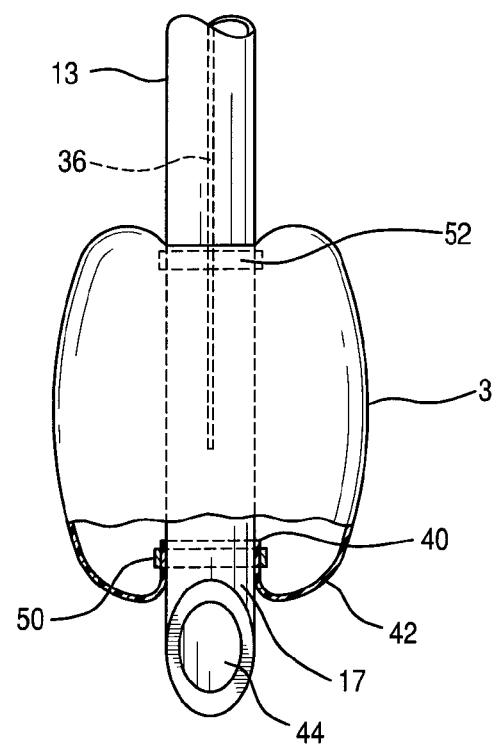
FIG. 2 is a schematic illustration of a distal end of an endotracheal tube in accordance with the present invention.

As shown in FIG. 2 two bands of radio-opaque material 50 and 52 are at or adjacent to the respective ends of the cuff 31 to define the opposite end regions thereof. In addition, the proximal end of tubular member 13 passes through and is secured to an oral bite piece 18 (FIG. 1). For example, a shaped end is received in the patient's mouth. This bite piece 18 may also include a second passageway 80 and is made of any suitable material.

By using a longer cuff and about a ¼ inch turn back upon itself, the upper portion of the cuff forms a cavity 55 or basin for accumulating bacteria or secretions that are then removed by a suction catheter or the like. The opposite end of the cuff is adjacent the beveled end of the tube and is also folded over upon itself but only by about ¼ of an inch for centering the tube in the airway. In addition, any minor channels for inflating the cuff or suctioning off secretions is placed in a portion of the tube with the greater radius i.e. under tension as opposed to compression to reduce or eliminate the likelihood of kinking. The wall thickness of the silicone tube is also of sufficient thickness to avoid kinking of the main passageway or airway and may be made thin with a D-shaped reinforcement.

In a preferred embodiment of the invention, an endotracheal tube 11 includes a thickened wall portion on an inner side of a curved portion thereof. The thickened wall portion is adjacent to the curve with a smaller radius i.e. that portion of the curve that is under compression. Further, with respect to endotracheal tubes that are made of a material other than a medical grade silicone, it may be necessary to incorporate a thin strip material to reduce the likelihood of kinking when the tube reaches a temperature of about 97° F. That strip may include a curved surface between the sides thereof for added resistance to kinking.

A prior art endotracheal tube 70 shown in FIG. 5A includes a thicker wall portion as defined by a D-shaped inner cross-section 76 and an outer circular cross-section with a major passageway passing through the tube 70 with the thicker portion of the wall section in an upper portion, this portion is under tension which reduces the likelihood of a minor lumen 75 kinking. However, in the present invention an endotracheal tube 80 as shown in FIG. 5B includes a thicker wall section 86 in a lower portion that is under compression and having the shaper radius, there is less chance of the major passageway kinking. As shown, the minor lumen for removing secretions is in the portion of the wall that is under tension.

While the invention has been described in connection with its accompanying drawings it should be recognized that changes and modifications may be therein without departing from scope of the appended claims.

What is claimed is:

1. A kink resistant endotracheal tube with an inflatable cuff for positioning said endotracheal tube in a patient's bronchia, said endotracheal tube comprising:

a flexible elongated tubular member having distal and proximal open ends, a beveled tip at said distal end and a curved portion between said distal and proximal ends, and said tubular member defining a central major passageway for ventilation of a patient;

a first minor passageway and an inflatable cuff for centering said tubular member in a patient's trachea and for accumulating secretions above said cuff and wherein said inflatable cuff is of a gas impervious material secured to an exterior surface of said tubular member at the distal end adjacent said beveled tip and at an upper portion a short distance above said distal end; and wherein said inflatable cuff is folded over upon itself at said upper portion to form a concave area for pooling secretions above said cuff;

wherein said inflatable cuff is folded over upon itself for a distance of about ¼ inch at said upper portion to form a concave area for pooling secretions above said cuff.

2. A kink resistant endotracheal tube according to claim 1 which includes a second minor passageway and a suction eye at a distal end of the greater radius thereof adjacent said upper portion and means generating suction in said second minor passageway for removing secretions from above said inflatable cuff; and in which said inflatable cuff is folded back upon itself by a distance of about ¼ inch in a lower area adjacent said beveled tip for centering said distal end in a patient's trachea.

3. A kink resistant endotracheal tube according to claim 2 in which said tubular member is formed of non-toxic material that is heat stable in its physical characteristics within the range of human body temperature to be encountered in use, has a hardness of about 80 durometers and an inside diameter to wall thickness ration of about 8:1 so that the member is non-collapsible during intubation and while in place in the trachea and capable of withstanding a 90 degree bend without collapsing.

4. A kink resistant endotracheal tube according to claim 3 in which said curved portion defines an inner pathway wherein said tubular member is under compression and an outer pathway wherein said tubular member is under tension and wherein said first and said second minor passages are disposed in the portion of said tubular member that are under tension.

5. A kink resistant endotracheal tube according to claim 4 in which said inflatable cuff is made of silicone.

6. A kink resistant endotracheal tube with an inflatable cuff for positioning said endotracheal tube in a patient's trachea, said endotracheal tube consisting of:
   a flexible elongated tubular member having distal and proximal open ends, a beveled tip at said distal end and a curved or straight portion between said distal end and said proximal end; and said tubular member being formed of non-toxic material that is heat stable in its physical characteristic within the range of human body temperature to be encountered in use, has a hardness of about 80 durometers, and an inside diameter to wall thickness of about 8:1 so that the member is non-collapsible during intubation and which in place in the trachea is capable of withstanding a 90 degree bend without collapsing; and
   said tubular member defining a central major passageway for ventilation of a patient, a first minor passageway and an inflatable cuff for centering said tubular member in a patient's trachea and for accumulating secretions above said cuff and wherein said inflatable cuff is of a gas impervious material secured to an exterior surface of said tubular member at said distal end adjacent said beveled tip and at an upper portion a relatively short distance above said distal end and wherein said inflatable cuff is folded back upon itself at said upper and lower portions by about ¼ inch to form a concave area for pooling secretions above said cuff;
   and a suction tube communicating with said concave area; and
   wherein said curved portion defines an inner pathway wherein said tubular member is under compression and an outer pathway wherein said tubular member is under tension and wherein said first and said second minor passageways are disposed in said portion of said tubular member that is under tension.

7. A kink resistant endotracheal tube according to claim 6 that further consists of said inflatable cuff being folded over upon itself by about ¼ inch at said distal end.

8. A kink resistant endotracheal tube according to claim 6 which includes a thickened wall in an area of said curved portion that is under compression.

9. A kink resistant endotracheal tube according to claim 6 that includes a reinforcing strip in an area of said curved portion that is under compression or a D-shaped reinforcement.

* * * * *

UNITED STATES PATENT AND TRADEMARK OFFICE
CERTIFICATE OF CORRECTION

PATENT NO. : 8,225,795 B2
APPLICATION NO. : 12/568230
DATED : July 24, 2012
INVENTOR(S) : Donald M. Pell Page 1 of 2

It is certified that error appears in the above-identified patent and that said Letters Patent is hereby corrected as shown below:

In the Specification

In the Description of the Preferred Embodiments of the Invention:
Column 3 Line 65, a reference numeral --63-- should be inserted after the term reinforcing strip; and
Column 3 Line 66, a reference numeral --60-- should be inserted between the word portion and the word that.
Column 4 Line 14, the second reference numeral '4' should be replaced with --4'--;
Column 4 Line 30, the word 'block' should be replaced with the word --piece--, and a reference numeral --18-- should be inserted following the word --piece--.
Column 5 Line 29, the reference numeral '16' should be replaced with a reference numeral --17--;
Column 5 Line 30, the reference numeral --31-- should be inserted between the word cuff and the word of;
Column 5 Line 31, the reference numeral '31' before the word of should be deleted;
Column 5 Line 32, the word 'Cuff' should be replaced with the text --Expandable cuff 31--;
Column 5 Line 33, the word --expandable-- should be inserted between the words the and cuff;
Column 5 Line 35, the word --expandable-- should be inserted between the words the and cuff;
Column 5 Line 36, the word "tracheal" and the reference numeral "19" should be deleted and replaced with the word --trachea--;
Column 5 Line 39, the word 'and' should be replaced with the word --of--;
Column 5 Line 43, the word --expandable-- should be inserted between the word the and the word cuff; and
Column 5 Line 48, the reference numeral '80' should be replaced with the reference numeral --82--.
Column 6 Line 4, the word --of-- should be inserted between the word strip and the word material;
Column 6 Line 4, the reference numeral --63-- should be inserted between the word material and the word to;
Column 6 Line 10, the reference numeral --73-- should be inserted between the word cross-section and the word with;
Column 6 Line 11, the reference numeral --20-- should be inserted between the word passageway and the word passing;

Signed and Sealed this
Twenty-sixth Day of May, 2020

Andrei Iancu
*Director of the United States Patent and Trademark Office*

Column 6 Line 12, the reference numeral --28-- should be inserted between the word portion and the word of;

Column 6 Line 17, the reference numeral --21-- should be inserted following the word passageway; and Column 6 Line 18, the reference numeral --85-- should be inserted following the word lumen.